United States Patent [19]
DiMatteo

[11] Patent Number: 4,787,239
[45] Date of Patent: Nov. 29, 1988

[54] SENSOR FOR HAND HELD GAS CHROMATOGRAPH

[75] Inventor: Richard DiMatteo, San Jose, Calif.

[73] Assignee: Mark Products, Inc., Sunnyvale, Calif.

[21] Appl. No.: 142,120

[22] Filed: Jan. 11, 1988

[51] Int. Cl.$^4$ ............................................ G01N 30/66
[52] U.S. Cl. .................................... 73/23.1; 73/27 R
[58] Field of Search ..................... 73/23.1, 27 R, 40.7; 55/67, 197, 386; 422/89; 436/161

[56] References Cited

U.S. PATENT DOCUMENTS

| | | | |
|---|---|---|---|
| 2,687,036 | 8/1954 | Minter | 73/27 R |
| 3,447,360 | 6/1969 | Laseter | 73/23.1 |
| 3,714,421 | 1/1973 | Josias et al. | 73/23.1 X |
| 3,717,028 | 2/1973 | Annino et al. | 73/23.1 |
| 3,786,675 | 1/1974 | Delatorre et al. | 73/27 R |
| 4,229,968 | 10/1980 | Muldoon | 73/23.1 |
| 4,648,260 | 3/1987 | Zuckerman | 73/23.1 |

FOREIGN PATENT DOCUMENTS 787974  12/1980  U.S.S.R. ..................... 73/23.1

Primary Examiner—Stewart J. Levy
Assistant Examiner—Joseph W. Roskos
Attorney, Agent, or Firm—Townsend and Townsend

[57] ABSTRACT

A portable gas chromatographic detector includes two identical platinum coils mounted on identically aligned conducting posts. One coil is placed in an occluded chamber; the other coil is placed in an identical isolated chamber. Both coils have connection to legs of a bridge circuit and have substantially identical current flow passed along their length. Both chambers are preferably identically dimensioned and are large enough not to interfere with the field of the coils. The occluded chamber communicates through a short passageway with a passing classified gas stream from a chromatographic column. It has been found that the motion with respect to one coil is compensated with respect to the motion with the remaining coil so that the only differential in electrical resistance measured across the bridge circuit is that induced by the cooling property of helium on the heated coil in the occluded chamber. Cycling of the portable chromatograph includes a first short cycle. In the absence of detected helium, the instrument immediately returns to a standby state in readiness for a closely repeated cycle. Upon the detection of helium, a second and longer cycle results prolonged only by that time interval necessary for measurement of the helium and purging helium residual from the instrument collection conduits. For rich helium measurement resulting in super cooling of the occluded coil, a reverse bias is applied to the isolated coil through the bridge circuit to induce a warming current charge to the supercooled occluded coil. This enables rapid repeated measurement without prolonged warm-up intervals which would be otherwise required.

8 Claims, 4 Drawing Sheets

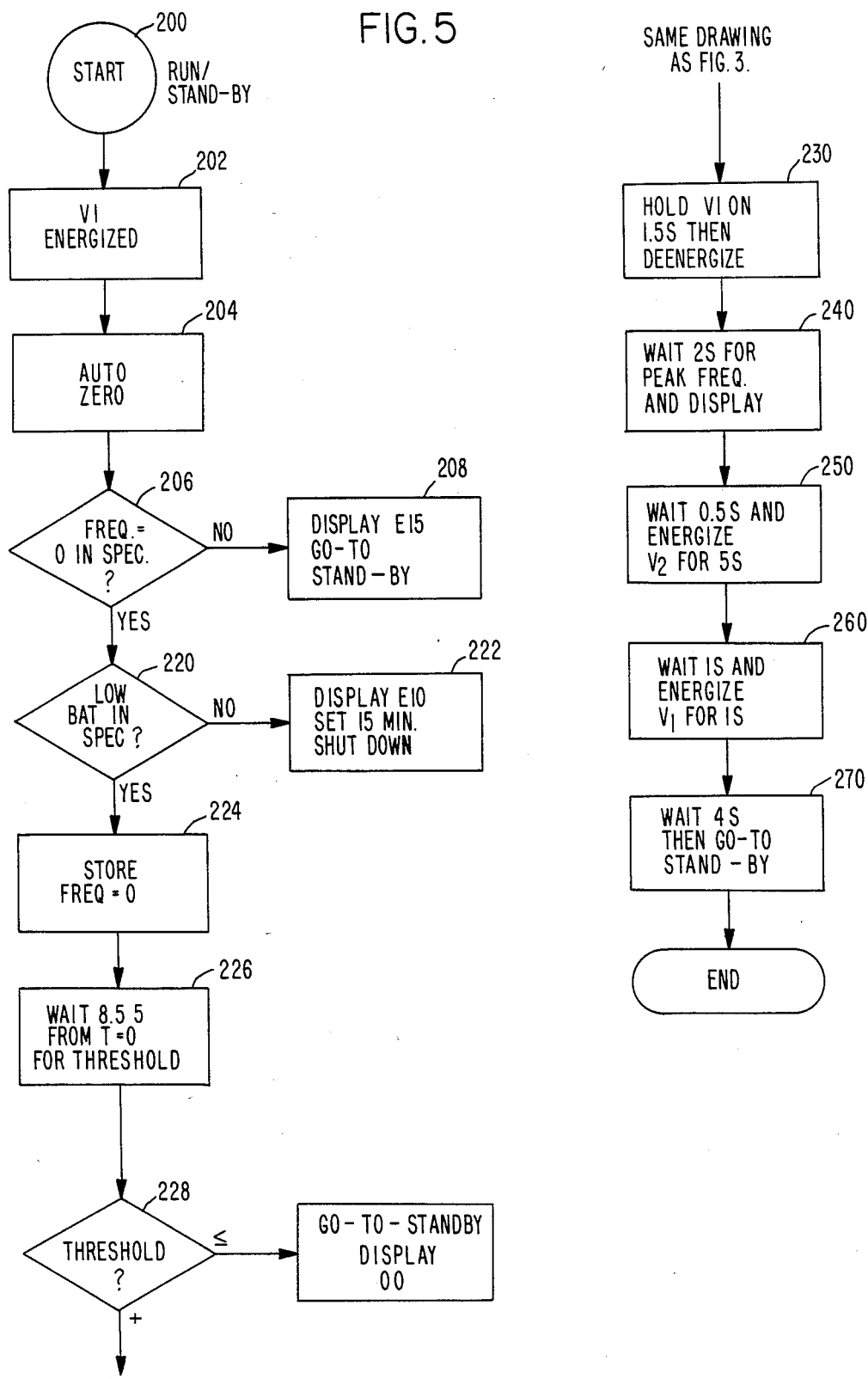

SENSOR FOR HAND HELD GAS CHROMATOGRAPH

This invention relates to chromatography and more particularly relates to a portable helium gas chromatograph having an improved detector and improved detection cycles.

Statement of the Problem

Helium is useful for the detection of underground leaks in utilities including underground gas lines, air pressurized telephone cables, pressurized vessels or any apparatus where containment is a consideration. In such tests, helium is either naturally present or introduced in the conduit to be tested. The helium is allowed to pass the length of the suspect line, either with a natural or induced flow rate.

Tuberculated underground lines allow the upward escape of helium. This helium rapidly rises upwardly and becomes detectable at the surface of the ground overlying the perforated pipe or conduit. The presence of helium is detected in trace amounts.

Assuming that these trace amounts of escaping helium can be located, the leaks in the pipe or conduit through which the trace amounts escape can likewise be located. Excavation and repair can be made with precision.

Conventional gas chromatographic equipment is not suitable for the detection of trace amounts of helium. Leak detection occurs in an industrial environment, usually a busy street. Instruments conventionally designed with long duration laboratory measurement cycles are unsuitable. Typically, both their elaborate calibration routines and long time intervals between successive measurements render their street usage unacceptable and impracticable. Most important, such instruments are not portable and indeed are subject to high degrees of inaccuracies when moved.

SUMMARY OF THE PRIOR ART

Zuckerman U.S. Pat. No. 4,648,260 issued March 10, 1987 to the assignee herein is an attempt to solve the problems related above. This device, which has met with commercial success, is not without difficulty.

Similar to the disclosure herein, the Zuckerman device includes paired electrodes across a bridge circuit. In that instrument, one electrode is open to the passing fluid stream while the other electrode is open to the atmosphere. Movement of the instruments result in inequality of resistance between the electrodes independent of helium being measured. Consequently, during such movement, inaccuracies are present to the extent of these inequalities.

In the commercial instrument practicing the Zuckerman disclosure both electrodes are now packed in dense felt trapped within concavities by a stainless steel screen. Unfortunately, such packing interferes with the electrodes equilibrating prior to measurement. Consequently, the instrument is subjected to continual drift and requires frequent recalibration during periods of continual use.

Further, conventional amplifiers are relied upon to measure in discrete amplification steps output from the measuring coil. These results when digitized likewise digitize in discrete steps. Consequently, there results an inability to measure trace amounts of helium less than 100 parts per million.

Finally, in that instrument, where high densities of helium are detected, a long recovery time is required between cycles. Periods of up to two or three minutes time are consumed. Such time period interferes with industrial leak detection.

SUMMARY OF INVENTION

A portable gas chromatograph for the detection of helium is disclosed which includes an improved detector of high sensitivity having reduced sensitivity to motion and a gas chromatograph cycle abbreviated to allow rapid helium detection at levels above 100 parts per million. The improved detector includes two identical platinum coils. The coils are mounted on identically aligned conducting posts. One coil is placed in an occluded chamber; the other coil is placed in an identical isolated chamber. Both coils have connection to legs of a bridge circuit and have substantially identical current flow passed along their length. The chamber for the occluded coil and the chamber for the isolated coil are preferably identically dimensioned and are large enough so that they in no way interfere with the field of the coils. The occluded chamber communicates through a short passageway with a passing classified fluid stream from a chromatographic column. It has been found that the motion with respect to one coil is compensated with respect to the motion with the remaining coil so that the only differential in electrical resistance measured across the bridge circuit is that induced by the cooling property of helium on the heated coil in the occluded chamber. Cycling of the portable chromatograph includes a first short cycle. In the absence of detected helium, the instrument immediately returns to a standby state in readiness for a closely repeated cycle. Upon the detection of helium, a second and longer cycle results prolonged only by that time interval necessary for measurement of the helium and purging helium residual from the instrument collection conduits. For rich helium measurement resulting in super cooling of the occluded coil, a reverse bias is applied to the isolated coil through the bridge circuit to induce a warming current charge to the supercooled occluded coil. This enables rapid repeated measurement without prolonged warm-up intervals which would be otherwise required.

Other Objects Features and Advantages

An object of this invention is to disclose an improved measurement cell having a reference electrode and a measurement electrode. Accordingly, two identical wire coils are utilized. The coils being preferably matched before being mounted to identically aligned coil supports. The coils on their supports are mounted in parallel relation each to its own identical chamber. These identical chambers have identical dimensions, identical alignments and are both large enough not to interfere with the electrical fields of the coils. One chamber and its contained coil is occluded; this chamber communicates to the passing classified gas stream to be measured by a single passageway. This passageway being utilized for both the entrance and exit of gas. The other chamber is isolated: the chamber does not directly communicate to any gas and the chamber walls effectively prevent the entrance and exit of gas (except by long term equilibration utilizing the porosity of the material defining the chambers). The detector is preferably used in a bridge circuit configuration.

An advantage of this electrode configuration is that the effects of motion on each of the identical electrodes is likewise identical. Consequently, minute imbalances caused by local molecular movement on one coil are duplicated by identical local molecular movement on the other coil. Consequently, motion effects on the coils cancel at the monitoring bridge circuit resulting in a differential output that is a function chiefly of helium induced coil cooling on the occluded coil.

A further object of this invention is to disclosure monitoring electronics capable of following minute differentials between the references and monitoring electrodes of this invention. According to this aspect, the differential signal of the bridge circuit is amplified to a single ended output and passed to a voltage to frequency converter. The resultant frequency (processed by a Schmidt trigger) is directly measured by the microprocessor with direct digital output relative to a previously and conventionally measured auto zero level.

An advantage of this aspect of the invention is that the incremental output of a conventional analog to digital converter is not present. Instead the disclosed protocol directly measures frequency differentials giving the instrument an overall sensitivity in the range of 10 parts per million with display preferably limited to 100 parts per million.

A further object of this invention is to disclose an instrument cycle that can be rapidly repeated. According to this aspect, the instrument includes two discrete cycles. One cycle is for when helium is not detected. The other cycle is for when helium is detected. Accordingly, when the instrument fails to indicate the presence of a threshold amount of helium, the measurement cycle is aborted and the instrument is immediately returned to standby status for taking the next sequential measurement, Where, however, helium is in fact detected, the instrument operation is prolonged to assure both accurate peak measurement of the acquired concentration of helium as well as through purging of all instrument conduits before the next sequential measurement.

An advantage of this aspect of the invention is that rapid sequential searches overlying suspected tuberculated lines can occur. Areas, such as streets having traffic, can be rapidly traversed. Only when leakage is detected is measurement restricted to lower cycle times required for accurate quantification of the outflowing helium and pinpointing of the suspected leak.

A further object of this invention is to disclose a cycling of the measurement electrode when high concentration of helium is encountered. Accordingly, when concentrations in excess of 70% by volume of helium are encountered, a back voltage is applied to the reference electrode during gas purging of the instrument. This back voltage on the reference electrode induces an enlarged current flow through the measurement electrode. This enlarged current flow through the measurement electrode enables reheating of the super cooled coil. This reheating enables rapid return of the measurement coil to equilibrium with the reference coil for the next sequential measurement.

An advantage of the entire operating circuitry disclosed with this chromatograph is that the instrument is capable of detecting for helium (as well as other light gases) in a continuous "sniffing" mode—a mode disclosed in prior art instruments. However, once a suspect gas is encountered, the instrument herein disclosed can revert to the disclosed batch testing mode. In this batch testing mode, the possibility of other gases causing electrode cooling can be eliminated.

A further advantage of this instrument with its new and improved sensor is the disclosed calibration procedure. This recalibration procedure can be periodically utilized to prevent drift that interferes with accurate measurement. At the same time, the disclosed sensor is less subject to drift than those sensors of the prior art.

BRIEF DESCRIPTION OF THE DRAWING

Other objects, features, and advantages of this invention can be more apparent after referring to the following specification in which:

FIG. 5 is a flow chart illustrating logic utilized.

Referring to FIG. 1, the improved detector D of this invention is disclosed. The detector consists of a ceramic block 14. The block has defined therein cylindrical chambers 12 and 12A. These chambers are side-by-side and identical.

Figure 1:
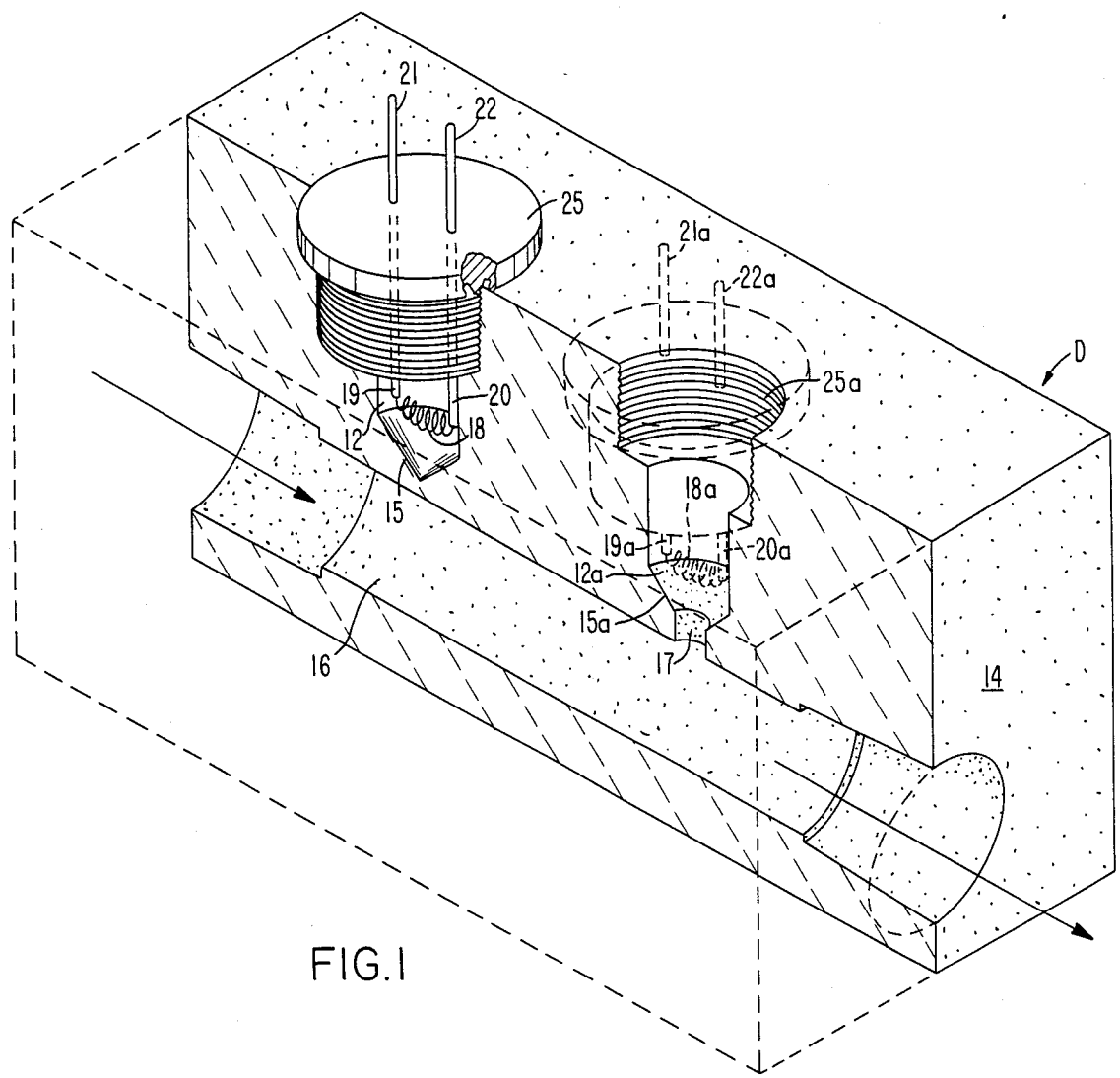
FIG. 1 is a perspective view, broken away, of the improved detector illustrating the isolated and occluded chambers with the identically aligned dimension and mounted coils therein.

Ceramic is preferred for the material of the block. Aluminum can be and has been used; it has the advantage of easy manufacture. Other similar materials may be used as well.

In the case of chamber 12, chamber 12 has a conical top 15 and is isolated from a passing gas stream in a conduit 16 defined with the block 14.

In the case of chamber 12A, it is communicated at its conical top via a conduit 17 to the passing gas stream in conduit 16 defined with block 14.

Each chamber includes a coil 18 and 18A. The coils are identical. Preferably they are wound with 17 turns from 0.001" wire with 0.002 coating of ceramic. The wire is composed of 90% platinum and 10% iridium. Before mounting of the coils 18, 18A: these coils are preferably matched. That is to say, they have an identical resistance.

Each coil is mounted on identical legs. Coil 18 is mounted between legs 19, 20. Coil 18A is mounted between legs 19A and 20A.

The legs are identically disposed and extend through an identical ceramic plug to their connectors protruding from the ceramic plug. Coil 18 has connectors 21. 22 protruding from plug 25. Likewise, coil 18A has connectors 21A, 22A protruding from plug 25A. Simply stated and viewing detector D, the reader may readily understand that everything about the chambers and their coils are identical.

Only one difference between the chambers exists. That difference is that gas passing through line 16 can communicate with chamber 12A through an occluded conduit 17. That is to say gas must both enter and exit from chamber 12A via the conduit 17.

It will be understood that ceramic is not an absolute atmospheric barrier. Thus, even though chamber 12 is isolated from the passing gas stream, long term equilibration of the inside and outside of the chamber can occur. For example, where the detector is moved to higher elevations and atmospheric pressure drops, equilibration of the atmosphere interior of chamber 12 to the exterior atmosphere will occur.

It will be understood that direct communication of chamber 12 to the exterior atmosphere is blocked.

Detector D is typically chosen from a ceramic having poor heat conducting properties. Thus, heat induced in the paired coils will be maintained in the coils and prevented from communication to the exterior atmosphere.

Chamber sides are chosen to have at least a signature volume. This signature volume is large enough so that intrusion does not occur to the electromagnetic fields present in the coils.

Construction is as follows. Typically, plugs 25 and 25A are identically matched with their respective coils 18 and 18A. Thereafter the plugs 25 and 25A are mounted within and sealed to the block of detector D, typically by conventional O-ring seals. It is important to note that the coils are identical in all respects. They are mounted to identical legs. They are placed in identical parallel alignment.

Figure 2:
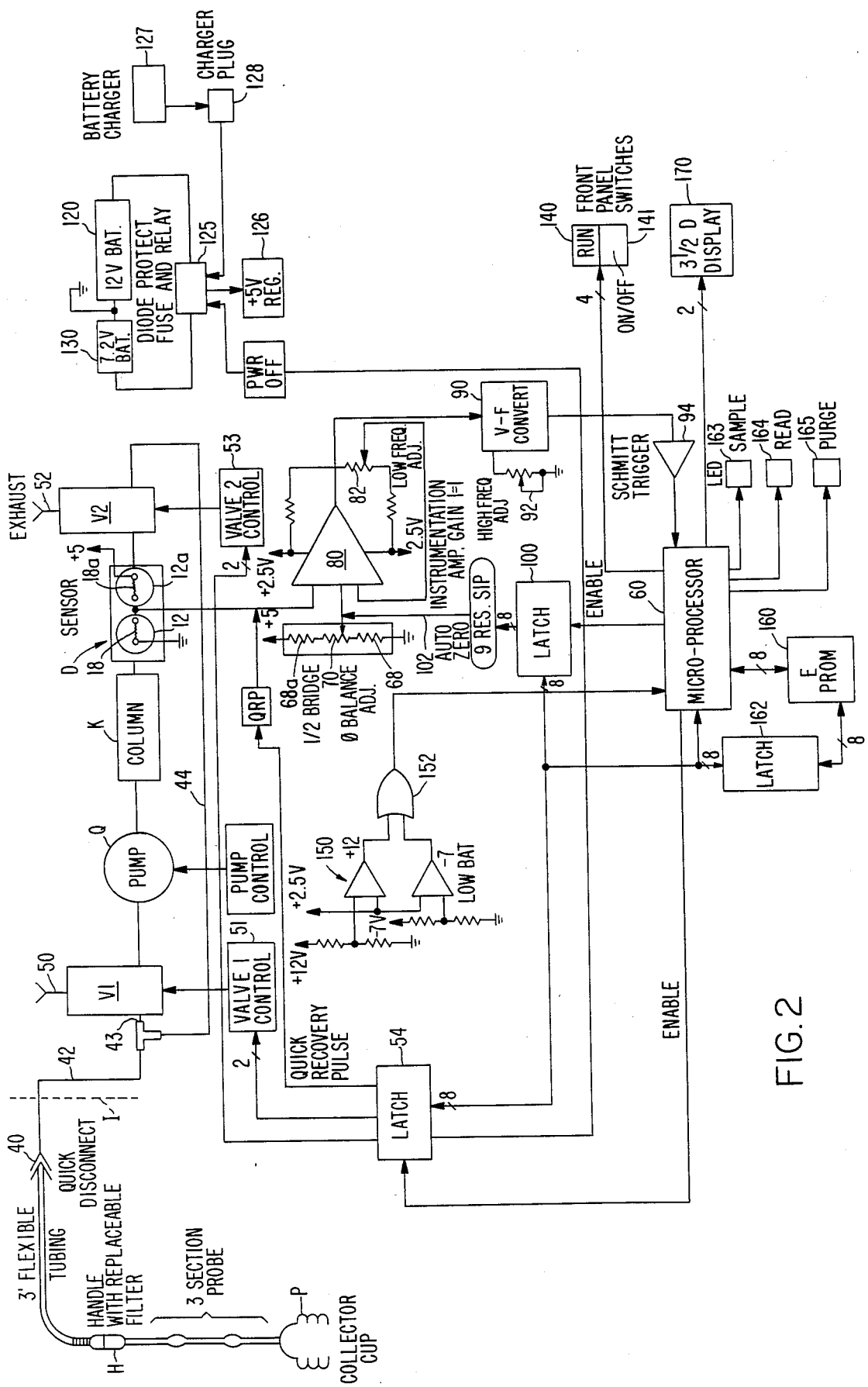
FIG. 2 is an operational schematic of the instrument including fluid flow lines and associated electrical conduits electronic control.

Having set forth the construction of the detector D, reference can now be had to the flow and electrical schematic of FIG. 2.

Referring to FIG. 2, a probe P having a handle H preferably incorporating a filter is connected at a quick disconnect 40 to a small portable chromatograph schematically denominated at the broken lines I. It will be understood that all fluid and electrical circuitry shown within FIG. 2 to the right of line I is contained in a small and portable casing.

The chromatograph includes a conduit 42 passing collected gas through valve V1, a pump Q, a chromatographic column K, sensor block D and valve V2. A second flow line 44 from valve V2 back to conduit 42 is used for purging the probe P and its connected conduits upon helium measurement.

Each of the valves V1, V2 is a three way valve. In a first and open position, flow passes directly through the valve. In a second and closed position, flow from the inlet side of the valve communicates through exhaust openings 50 in the case of valve V1 and 52 in the case of valve V2.

The valves are of the type wherein a first pulse opens the valves for through flow and a second maintenance pulse of lower energy maintains the valve in the open state.

Valve control is conventional. Typically, a valve control circuit 51 for valve V1 and 53 for valve V2 connects through a latch 54 which latch is enabled by a microprocessor 60.

The detector is wired in a bridge circuit. The electrode 18 in chamber 12 is communicated to ground whereas the electrode 18A in chamber 12A is communicated to a 5 volt source. Naturally, the bridge upon initial installation must be balanced. Consequently, bridge resistances 68 and 68A are adjusted at an adjusting pot 70. The imbalance between the respective bridges is measured across an instrumentation amplifier 80.

Instrumentation amplifier 80 has a 1 to 1 gain. Its sole purpose is for the conversion of the double ended differential output to a single ended voltage output. This amplifier includes a low frequency adjustment 82 for initial calibration.

Output of differential amplifier 80 occurs to a voltage to frequency converter 90. This converter has connected thereto a high frequency adjustment 92.

The voltage to frequency converter is manufactured by Analog Devices of Norwood, Mass., and is vended under the description AD654JN. The instrumentation amplifier utilized herein is manufactured by the General Electric Intersil Division of Cupertino, Calif. and vended under the designation ICL 7605 CJN. Remaining electronic components are conventional.

An auto zero circuit enabled through a latch 100 at line 102.

Paired batteries including 12 volt battery 120 and 7.2 volt battery 130 pass through protect diodes, fuse, and relay 125 powering a 5 volt regulator 126 for power utilized throughout the circuit. Provision is made for charging at a charger 127 through plug 128. A panel run switch 140 and on/off switch 141 is utilized. Since the on-off switches are of a relay type, a low battery circuit 150 connected through NOR gate 152 times out the instrument operation so that a low battery condition does not lock the instrument in an "on" position.

The microprocessor includes an E prom memory 160 addressed by latch 162. Light emitting diodes 163 indicates the taking of a sample. Light emitting diode 164 indicates a read state of the instrument. Light emitting diode 165 indicates a purge state of the instrument. Thus, the operator of the instrument is informed of the instruments operating condition, Readings are output to a digital display 170.

In order to have the microprocessor accurately read frequency output at the voltage to frequency converter, a Schmidt trigger 94 is utilized. This Schmidt trigger converts the 90% rise time of the frequency output to an interval of less than 50 nanoseconds from a range in the order of 200 nanoseconds. As is well known in the art, such conversion enables microprocessor 60 to adequately count the frequency pulses.

It will be understood that pump Q is a constant displacement pump which is technically calibrated at the factory. Preferably, a 7 cc/minute flow rate is utilized. All collection and exhaust conduits are appropriately sized with respect to the flow rates hereinafter set forth to ensure purging in accordance with the timing cycle illustrated with respect to FIG. 3.

Only brief reference will be made to FIG. 4.

Figure 4:
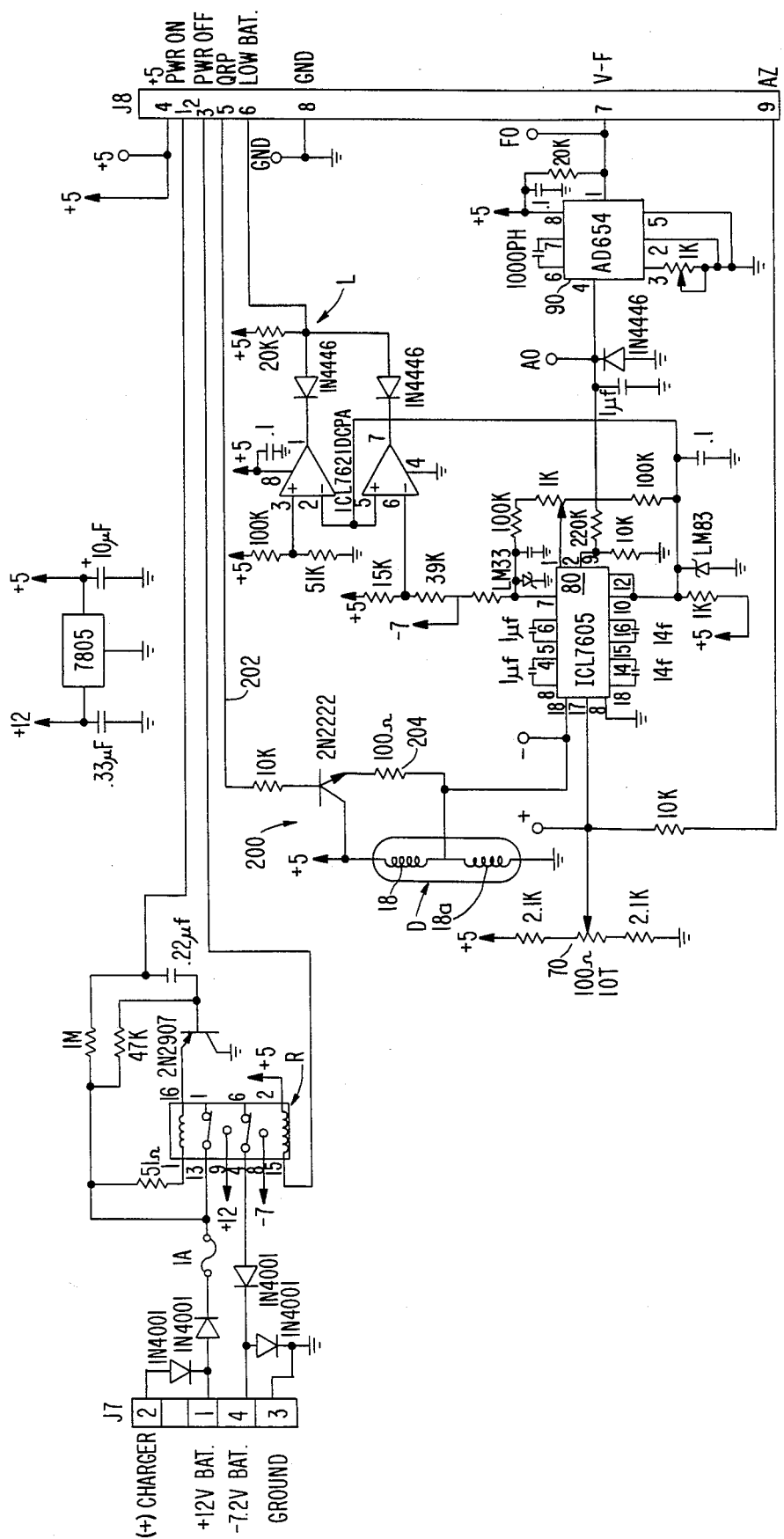
FIG. 4 is an isolated schematic illustrating a circuit for back biasing the isolated coil to induce a warming current flow through a super cooled coil.

FIG. 4 illustrates the powered relay R and the low battery detection circuit L. The reader will understand that these respective circuits are conventional with the attached microprocessor terminating instrument operation upon detection of the low battery condition.

FIG. 4 illustrates the novel, quick recovery pulse circuit 200 used with this invention.

Detector D is schematically illustrated having measurement coil 18A and reference coil 18. Upon supercooling of coil 18A and a measurement of a helium concentration in excess of 70%, a pulse at line 202 back biases bridge resistance 204 to cause an excess current flow through coil 18A. Such back biasing in the circuit herein occurs for a period of three seconds, a time interval to bring measurement electrode 18A near to a thermal equilibrium with its reference electrode 18 after measuring helium concentrations in excess of 70%.

Having set forth the operative conduits and electrical connections, timing of the instrument operation will now be discussed. Specific programming of EPROM 160 will be left to the routineer from the disclosures of FIGS. 3 and 5.

Referring to the software logic diagram upon start 200. V1 is energized to the open position (202). An auto zero 204 is performed.

Where a frequency in excess of the predetermined limit over auto zero is not encountered, the instrument returns to the standby state at 208. This state includes valve V1 being energized and the auto zero reading being maintained.

Figure 3:
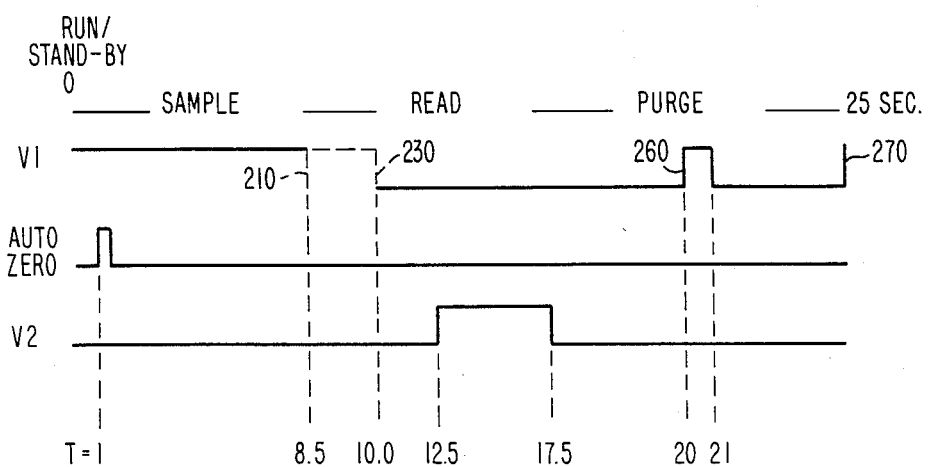
FIG. 3 is a timing diagram illustrating a truncated cycle where no helium is detected and an elongated cycle where helium is, in fact, detected.

Referring to FIG. 3, each time a measurement is undertaken, the instrument cycles for 8.5 seconds. During this cycle and referring to FIG. 2, valve V1 is open permitting air flow through probe P, handle H, conduit 42, pump Q, column K and detector D with exhaust through closed valve V2 at exhaust port 52. This portion of this instrument cycle is repeated until helium is detected.

The program is provided with an interrupt. Specifically, and upon low battery at 220 (reference FIG. 5) the program times out instrument operation in 15 minutes and inhibits during this period of time further readings from being made.

Providing that 206 and 220 are in a predetermined specification, the frequency set by auto zero is stored at 224.

Assuming helium is detected, the instrument at 230 holds valve V1 on for 1.5 seconds. Thereafter, valve V1 is off. (See FIG. 2) In the off state intake to the measuring fluid circuit occurs through port 50 instead of conduit 42. Helium will still be passing through the column K and detector D, Consequently, a 2 second delay in reading occurs.

Valve V2 is opened at 12.5 seconds into the measurement cycle. When valve V2 is open, flow occurs in port 50 of valve V1 through pump Q, column K, detector D and around conduit 44. At conduit 44 gas is discharged in a reverse path through conduit 42, disconnect 40, handle H and probe P. Complete purging of the system occurs in order to rid the system of residual helium.

At 17 seconds into the measurement cycle, valve V2 is again opened. At this time, outflow at port 52 occurs.

It can be seen that a small occluding tube 43 exists when valve V2 is open purging the system through conduit 44. To prevent any trapping of measured helium. valve V1 is briefly opened for a one second interval at time 20 (see 260 FIGS. 3 and 5). Finally, normal purging at 270 of the system continues for a remaining four seconds.

The reader will thus understand that there are constituted two discrete cycles. One cycle wherein helium is not detected in sufficient quantity is 8.5 seconds long. This cycle enables an instrument operator to move immediately to a next sample site. By the time the operator arrives at the next site, the instrument is ready to detect for the possible presence of helium in an additional 8.5 second cycle.

Alternately, and where a leak is detected, instrument cycle time occurs over a period of 25 seconds. This cycle time coincides with the urgency required for more careful measurement in order to pinpoint the possible leaks.

The reader will understand that the disclosed circuitry is ideal when used in combination with helium monitor of the continuous type. By simply having the monitor continuously look for gases causing thermal conductivity, the incident of thermal conductivity can be detected in the sample. Thereafter by having the instrument operate in the disclosed batch sampling mode, the presence of helium can be discriminated out from other gases. For example, it has been found that 5000 ppm of methane or ethane is required to give the same thermal conductivity of 100 ppm helium. It will thus be realized that helium will not only be detected in a continuous operating mode—but that it will be readily discriminated from all other candidate gases by the batch sample apparatus herein set forth.

What is claimed is:

1. In combination with a portable helium detector having a probe for gathering a gas sample, a chromatographic column for classifying helium in a passing gas stream from said gathered sample, a detector cell having communication to said passing gas stream and including a reference electrode and a measurement electrode, and a circuit having input to said electrodes and an output for amplification of the differential output of said reference electrode with respect to said measurement electrode: and means for digitizing the output of said circuit, the improvement in said detector cell comprising:

a detector cell body defining first and second identical cavities for confining said electrodes;

first and second identical electrode assemblies, each electrode assembly including identical first and second legs, identical coils mounted between said legs, said legs mounted to identical bases configured to seal the cavities in said detector cell body:

said first electrode assembly constructed to dimensionally and electrically match said second electrode assembly:

said first and second electrode assemblies placed in said detector cell at said bases to seal said electrodes within said first and second cavities:

said first and second electrode assemblies having identical alignment in said cells as sealed with said first and second legs and said coils being disposed in parallel alignment whereby motion induced changes in electrical resistivity of said coil is substantially identical for both cells:

one of said cavities defining a single passageway for occluded sampling of a passing classified gas stream from said columns: and the other of said cavities isolated for the prevention of sampling of said classified gas stream from said column.

2. The invention of claim 1 and wherein said electrodes are connected in a bridge circuit for the detecting of electrical differential between said coils.

3. The invention of claim 2 and including means for biasing one of said legs of said bridge circuit for inducing in said electrode in said cavity defining a single passageway for occluding sampling an increased current for equilibrating said electrode when said electrode is supercooled by said helium.

4. In combination with a portable helium detector having a probe for gathering a sample, a column for classifying to the front of said gathered sample helium in a passing gas stream; a detector cell having communication to said passing gas stream and including a reference electrode and a measurement electrode: and a circuit having input to said electrodes and output for amplification of the differential output of said reference electrode with respect to the said measurement of said electrode; and means for digitizing the output of said circuit, the improvement to said circuit comprising:

bridge circuit means having said reference electrode connected to one of said legs and said measurement electrode connected to the other of said legs:

an amplifier connected across said bridge circuit for receiving the differential of said bridge circuit and outputting said differential as a voltage;

a voltage to frequency converter for outputting a frequency which is proportional to said voltage: and, a microprocessor for measuring said frequency to determine the differential and resistance of said electrodes of said detector.

5. The invention of claim 4 and including a Schmidt trigger, said Schmidt trigger disposed between said voltage to frequency converter and said microprocessor for increasing the rise time of frequency output by said voltage to frequency converter.

6. An improvement to a process cycle for a helium detector said process cycle having the steps of providing a probe for gathering a gas sample including suspected helium:

providing a column for classifying helium to the leading edge of said gas sample gathered by said probe, said column having an input for receiving said sample and an output for discharging said sample;

providing a detector connected to said column output for measuring the thermal conductivity of passing gas stream to indicate the suspected presence of helium;

providing a pump to move said sample through said probe column and detector for the determination of the presence of helium in said sample:

providing valve means for flushing said probe upon measurement of helium in said sample;

running said pump for a sufficient interval of time to pass said sample through said probe column and detector to measure helium in said sample:

operating said valve to flush said probe of helium:

the improvement to said cycle including the steps of:

monitoring said detector for a sufficient period of time to determine the absence of helium: and aborting said operation of said valve to flush said probe when helium is not detected.

7. The invention of claim 6 and including the further improvement of shortening said run time of said pump when the absence of helium is observed in said detector.

8. In combination with a portable helium detector having a probe for gathering a sample, a column for classifying helium to the front of said gathered sample in a passing gas stream; a detector cell having communication to said passing gas stream and including a reference electrode and a measurement electrode: a circuit having input to said electrodes and output for amplification of the differential output of said reference electrode with respect to said measurement electrode: and means for digitizing the output of said circuit, the improvement in said circuit including:

means operably connected to said detector for determining a helium abundance above a level of 70%:

means in said circuit for applying an electrode potential across said measurement electrode after sample of said helium abundance for equilibrating said measurement electrode to said reference electrode immediately after cooling by said abundance of helium.

* * * * *